United States Patent [19]

Heiss

[11] Patent Number: 4,519,953

[45] Date of Patent: May 28, 1985

[54] PROCESS FOR PREPARING STILBENEDICARBONITRILES

[75] Inventor: Lorenz Heiss, Hofheim am Taunus, Fed. Rep. of Germany

[73] Assignee: Hoechst Aktiengesellschaft, Frankfurt, Fed. Rep. of Germany

[21] Appl. No.: 594,547

[22] Filed: Mar. 29, 1984

[30] Foreign Application Priority Data

Apr. 2, 1983 [DE] Fed. Rep. of Germany ....... 3312164

[51] Int. Cl.$^3$ .......................................... C07C 121/64
[52] U.S. Cl. ................................................ 260/465 H
[58] Field of Search ..................................... 260/465 H

[56] References Cited

U.S. PATENT DOCUMENTS 2,688,631  9/1954  Toland, Jr. ..................... 260/465 H Primary Examiner—Dolph H. Torrence
Attorney, Agent, or Firm—Connolly and Hutz

[57] ABSTRACT

A process for preparing stilbenedicarbonitrile by dimerizing o- or p-cyanobenzyl chloride in a polar aprotic solvent in the presence of an excess of alkali metal hydroxide powder. Stilbenedicarbonitriles are precursors for the preparation of fluorescent brighteners of the bisbenzoxazolylstilbene class.

1 Claim, No Drawings

PROCESS FOR PREPARING STILBENEDICARBONITRILES

There is no known industrially practicable method of synthesizing stilbenedicarbonitrile. Toland et al., in U.S. Pat. No. 2,688,631, describe a process in which p-tolunitrile is dimerized at 260°–300° C. in the presence of sulfur with loss of hydrogen and the yields are very low. The process described by P. Walden in Ber. D. Chem.Ges. 23 (1890), 1959, for the preparation of dinitrostilbene from p-nitrobenzyl chloride in alcoholic potassium hydroxide solution does not lead to the stilbene compound in the case of p-cyanobenzyl chloride.

It has now been found, surprisingly, that very pure stilbenedicarbonitriles can be obtained in high yields by reacting readily accessible o- or p-cyanobenzyl chloride at about room temperature with stirring in aprotic solvents with an excess of alkali metal hydroxide powder. The reaction is advantageously carried out in an inert nitrogen atmosphere and under exclusion of moisture and with as finely pulverulent dry alkali metal hydroxide as possible. The chief candidate for use as the aprotic polar solvent is dimethylformamide. The reaction is carried out at room temperature until all the organic chlorine has reacted. The reaction generally takes 6 to 12 hours. When the reaction is complete the reaction mixture is acidified, preferably with anhydrous organic acids, such as, for example, glacial acetic acid, and is filtered with suction, and the filter residue is washed with solvent and then with water until chloride ions are no longer detectable. Stilbene-4,4'-dicarbonitrile or stilbene-2,2'-dicarbonitrile, respectively, is obtained in the form of white crystals in yields above 80%.

These stilbene compounds can be hydrolyzed to stilbenedicarboxylic acid, which can be used for preparing bisbenzoxazolylstilbenes which are used as fluorescent brighteners.

EXAMPLE 1

24 g (0.6 mole) of sodium hydroxide powder are dispersed in 100 g of dimethylformamide at the same time as nitrogen is passed in, and 30.4 g (0.2 mole) of p-cyanobenzyl chloride are added at 20° C. The mixture is stirred for about 6–12 hours until all the organically bound chlorine has reacted, and 30 g (0.5 mole) of glacial acetic acid are then added. When the mixture has cooled down to 0° C. it is filtered with suction, and the filter residue is washed with dimethylformamide and then with water until no chloride ions are detectable in the water from the wash. Drying gives 18.9 g of stilbene-4,4'-dicarbonitrile in the form of white crystals.

Yield: 82%, Melting point: 288° C.

| C | 83.5% calculated; | 83.3% found |
| H | 4.3% calculated;  | 4.3% found  |
| N | 12.2% calculated; | 12.1% found |

EXAMPLE 2

30.4 g (0.2 mole) of o-cyanobenzyl chloride are dissolved in 70 g of dimethylformamide, and 24 g (0.6 mole) of sodium hydroxide powder are added at the same time as nitrogen is passed in. The mixture is stirred at 20° C. for about 6–10 hours until all the organically bound chlorine has reacted, 70 g of methanol are added dropwise, and the precipitate is filtered off with suction at 0° C. and is washed with methanol and then with water until no chlorine ions are detectable in the water from the wash. Drying gives 17.8 g of stilbene-2,2'-dicarbonitrile in the form of white crystals.

Yield: 77.5%, Melting point: 187°–189° C.

| C | 83.5% calculated; | 83.1% found |
| H | 4.3% calculated;  | 4.3% found  |
| N | 12.2% calculated; | 12.0% found |

What is claimed is:

1. A process for preparing stilbenedicarbonitriles which comprises dimerizing o- or p-cyanobenzyl chloride in a polar aprotic solvent in the presence of an excess of alkali metal hydroxide powder with loss of hydrogen chloride.